United States Patent [19]

Roberts et al.

[11] Patent Number: 5,723,696
[45] Date of Patent: Mar. 3, 1998

[54] PROCESS FOR THE PRODUCTION OF POLYGLYCEROLS

[75] Inventors: Glyn Roberts, Wirral Merseyside; Alan Reginald Minihan, Merseyside, both of Great Britain; Johannes Arie M. Laan, Breda; Johan Jan W. Eshuis, Schiedam, both of Netherlands

[73] Assignee: Unichema Chemie B.V., Gouda, Netherlands

[21] Appl. No.: 676,247

[22] PCT Filed: Jan. 24, 1995

[86] PCT No.: PCT/EP95/00248

§ 371 Date: Jul. 17, 1996

§ 102(e) Date: Jul. 17, 1996

[87] PCT Pub. No.: WO95/21210

PCT Pub. Date: Aug. 10, 1995

[30] Foreign Application Priority Data

Feb. 4, 1994 [EP] European Pat. Off. ............ 94300859

[51] Int. Cl.$^6$ .................................................. C07C 31/22
[52] U.S. Cl. ........................ 568/869; 568/678; 568/680
[58] Field of Search ........................ 568/678, 680, 568/869

[56] References Cited

FOREIGN PATENT DOCUMENTS

| 61-238749 | 10/1986 | Japan. |
| 1 156 709 | 7/1969 | United Kingdom. |
| 93/25511 | 12/1993 | WIPO. |

*Primary Examiner*—Gary Geist
*Assistant Examiner*—Sreeni Padmanabhan
*Attorney, Agent, or Firm*—Cushman Darby & Cushman IP Group Pillsbury Madison & Sutro LLP

[57] ABSTRACT

Glycerol, glycidol, glycerol carbonate or 2,2-dimethyl-1,3-dioxolane-4-methanol is polymerized into preponderantly linear oligomers at 150° C. to 350° C. in the presence of a catalyst, selected from RbF, CsF and/or KF impregnated on alumina and zirconium oxide. The alumina is preferably gamma-alumina.

8 Claims, No Drawings

PROCESS FOR THE PRODUCTION OF POLYGLYCEROLS

This is the U.S. National Stage Application of PCT/EP95/00248 filed Jan. 24, 1995 now WO95/21210 published Aug. 10, 1995.

The present invention relates to a process of preparing polymers of glycerol in which glycerol, or its derivatives glycidol, glycerol carbonate or isopropylidene glycerol (or 2,2-dimethyl-1,3-dioxolane-4-methanol) are polymerized in the presence of an effective amount of a catalyst.

Such a process is known from British Patent Specification GB-A-1,205,163 (Eastman Kodak Comp.) in which glycerol is condensed at 200° C. to 280° C. in the presence of an alkaline catalyst, such as the alkali metal or alkaline earth metal oxides, hydroxides, bicarbonates, carbonates and salts of fatty acids.

In Japanese Patent Application JP-A-61/238,749 (Nippon Oils and Fats Co. Ltd.) a process has been described of manufacturing polyglycerol with only small amounts of cyclic polymerization products. In this process glycerol is condensed at 240° C.–260° C. after addition of 0.1–5% by weight of alkali catalyst and the same amount of an aluminium oxide comprising adsorbent. Examples of the adsorbent of the aluminium oxide type are activated alumina, zeolite, synthetic adsorbents and activated clays. The zeolite should contain 5% by weight or more of aluminium oxide, but no more indication has been given about the type of the zeolite than that it was manufactured by Mizusawa Kagaku.

In our pending European Patent Application EP 93200356.9 (Unilever) we have described a process of polymerizing glycerol in the presence of an acid zeolite having an average pore size of at least 0.6 nm, in which process preponderantly cyclic polymers are formed. In comparative examples, glycerol is heated to polymerization temperature in the presence of zeolite Y in the sodium form, sodium mordenite or an acidic beta zeolite in the presence of sodium hydroxide, but in all these cases no polymer was formed.

In further investigations as to the role of catalysts in the polymerization of glycerol or its derivatives glycidol, glycerol carbonate and isopropylidene glycerol, it has been found that polymers of glycerol with an appreciable percentage of linear oligomers are obtained if glycerol or the said derivatives are polymerized in the presence of an effective amount of a catalyst, selected from the group consisting of: cesium fluoride impregnated on alumina, potassium fluoride impregnated on alumina, rubidium fluoride impregnated on alumina, zirconium oxide, cesium ions exchanged zeolite and rubidium ions exchanged zeolite. Preferably the alumina on which the RbF, CsF and/or KF has been impregnated is gamma-alumina. The zirconium oxide is preferably zirconium dioxide. The zeolite preferably is an Y-type zeolite or a zeolite beta.

Zeolites are crystalline alumina silicates of alkali metals or alkaline earth metals, represented by the general formula

$M_{2/n}O \cdot Al_2O_3 \cdot y\, SiO_2 \cdot wH_2O$

Where y=2 or greater, n is the cation valence and w represents the water contained in the zeolite. Particularly the so-called Y-zeolites and zeolites beta, which had been subjected to a cation exchange with cesium or rubidium ions appeared to be very effective catalysts in the polymerization of glycerol or its said derivatives. This is surprising, since the sodium form of the zeolites appeared to be inactive in the polymerization of glycerol. The preparation of rubidium (RbY) or cesium ion-exchanged zeolite Y (CsY) is effected in a manner known per se, such as for example described in Bull. Chem. Soc. Japan 59 (6), 1761–1765 (1986).

Also zeolites which have been subjected to cation exchange and impregnation by a mixture of rubidium and/or cesium ions and potassium ions may be used.

The alumina impregnated with rubidium fluoride and/or cesium fluoride and/or potassium fluoride is prepared in a manner known per se, for example as described in Bull. Soc. Chem. Japan 55 (8), 2504–2507 (1982). Also mixtures of rubidium or cesium and potassium fluoride may be used and the amount of fluoride may vary from 0.1 to 1.0 mole of CsF or KF, or more, impregnated on 100 g of alumina. The alumina preferably is gamma-alumina. The zirconium oxide may be zirconium dioxide or the at least partially hydrated zirconium dioxide as may be obtained in a manner known per se. Hydrous zirconia for example is precipitated when solutions of zirconium salts are treated with alkalies. The water is loosely bound and may be removed by drying.

The advantage of the use of solid, heterogenous catalysts is that the catalyst can relatively easy be separated from the oligomeric reaction product and that the catalyst can be regenerated. Also the obtained reaction product can at least partially be esterified in the presence of the same catalyst with saturated or unsaturated, straight or branched chain C2–C24 monocarboxylic acids.

Therefore, the present invention relates to a process of preparing polymers of glycerol in which glycerol, or its derivations glycidol, glycerol carbonate or isopropylidene glycerol (or 2,2-dimethyl-1,3-dioxolane-4-methanol) is polymerized in the presence of an effective amount of a catalyst, which is characterized in that the catalyst is selected from the group consisting of rubidium fluoride impregnated on alumina, cesium fluoride impregnated on alumina, potassium fluoride impregnated on alumina, zirconium oxide, cesium ions exchanged zeolite, and rubidium ions exchanged zeolite. Preferably the alumina is gamma-alumina and the zeolite preferably is an Y-zeolite or a zeolite beta.

The amount of catalyst used may vary over a wide range from about 0.5% by weight to 100% by weight based on the glycerol, glycidol, glycerol carbonate or isopropylidene glycerol, but preferably from 1% by weight to 10% by weight is used.

In effecting the reaction an inert gas atmosphere may be used, such as a nitrogen blanket. The temperature at which the reaction is effected varies from 150° C. to 350° C., although also somewhat lower temperatures may be used. Preferably, a temperature of from 180° C. to 250° C. is used. A very effective method of heating is the application of microwaves. The reaction may also be favourably influenced by the application of ultrasonic vibrations. In general, by selecting the optimum reaction conditions, the process according to the present invention particularly with cesium-zeolite provides polymerized glycerol having at least 50% by weight, based on the reaction mixture freed from non-polymerized glycerol, of linear oligomers of glycerol.

The invention will now further be illustrated on hand of the following examples.

EXAMPLE I 100 grams of glycerol was heated to 300° C. in the presence of 5 grams of cesium exchanged zeolite Y. During the reaction samples were taken and analysed.

Analysis of the product mixtures was carried out by gas chromatography (GC) on a Hewlett Packard 5880 apparatus, using a 50 cm×2 mm column packed with 3% OV-1 on gaschrom Q. A linear temperature programme was run from 100°–300° C. at a rate of 10° C./minute with an initial time of 10 minutes at 100° C. and a final time of 10 minutes at 300° C. Structural assignment was made by combined gas chromatography/mass spectrometry (CG/MS) on a Hewlett Packard 5970 B apparatus with the mass spectrometer operating in the electron impact mode, using a 10 m capillary CP-Sil 5 CB column. A linear temperature programme was run from 50°–275° C. at a rate of 5° C./minute with an initial time of 3 minutes at 50° C. and a final time of 20 minutes at 275° C.

For both GC and GC/MS, samples were analysed as the silyl derivatives by reacting them with a mixture of hexamethyldisilazane (30 parts) and trimethylsilyl-chloride (15 parts) in pyridine (100 parts) prior to injection.

The following data were obtained (in % by weight):

| Composition after: | 6 h. | 24 h. | 30 h. |
| --- | --- | --- | --- |
| Glycerol | 87 | 65 | 42 |
| Linear diglycerol | 10 | 27 | 35 |
| Linear triglycerol | — | 5 | 14 |
| Linear tetraglycerol | — | — | 4 |

The total amounts do not add up to 100% because the amounts were calculated from the gas chromatography and mass spectrometry.

EXAMPLE II 100 grams of glycerol were heated to 240° C. (±5° C.) in the presence of 10 grams of cesium exchanged zeolite Y, impregnated with 10% by weight (based on the zeolite) of cesium acetate. The following data were obtained, analysed as described in Example I (in % by weight):

| Composition after: | 6 h. | 22 h. | 30 h. |
| --- | --- | --- | --- |
| Glycerol | 82 | 69 | 57 |
| Linear diglycerol | 13 | 21 | 26 |
| Linear triglycerol | — | 4 | 7 |

EXAMPLE III

Example II was repeated, but now using 10 grams of cesium exchanged zeolite Y, impregnated with 50% by weight (based on the zeolite) of cesium acetate. The following data were obtained, analysed as described in Example I (in % by weight):

| Composition after: | 19 h. | 26 h. | 48 h. |
| --- | --- | --- | --- |
| Glycerol | 59 | 51 | 31 |
| linear diglycerol | 31 | 35 | 34 |
| Linear triglycerol | 6 | 10 | 17 |
| Linear tetraglycerol | — | 2 | 7 |
| Linear pentaglycerol | — | — | 3 |

From this example it is clear that if the oligomerization is effected for a prolonged time, the number of higher oligomers is increasing. Dependent on the required type of product, the oligomerization reaction can therefore be stopped or prolonged.

EXAMPLE IV 100 grams of glycerol were heated to 240° C. (±5° C.) in the presence of 2.5 grams of KF on gamma-alumina (comprising 40% weight of KF). After 7 hours of heating the composition of the reaction product was analysed as described in Example I as: 55 wt % glycerol, 35 wt % linear diglycerol and 9 wt % linear triglcyerol. After 22 hours of heating, however, a complex reaction mixture was obtained of the following composition (all in % by weight): glycerol 3; cyclic diglycerol 13; linear diglycerol 19; cyclic triglycerol 6; linear triglycerol 19; cyclic tetraglycerol 3; linear tetraglycerol 13; linear pentaglycerol 10 and linear hexaglycerol 10. Although more cyclic oligomer product is formed, the preponderance of the reaction product is still linear oligomer.

EXAMPLE V 100 grams of glycerol were heated to 240° C. (±5° C.) in the presence of 2.5 grams of zirconium dioxide. After 7 hours of reaction, the reaction product was analysed as described in Example I, and its composition was (in percent by weight): glycerol 51; cyclic diglycerol 2; linear diglycerol 28; cyclic triglycerol 2; linear triglcyerol 9 and higher oligomers 5.

We claim:

1. A process of preparing polymers of glycerol which comprises polymerizing glycerol, glycidol, glycerol carbonate or 2,2-dimethyl-1,3-dioxolane-4-methanol in the presence of an effective amount of a catalyst selected from the group consisting of: rubidium fluoride impregnated on alumina; cesium fluoride impregnated on alumina; potassium fluoride impregnated on alumina; and zirconium oxide.

2. A process according to claim 1, in which the alumina is gamma-alumina.

3. A process according to claim 1, in which the zirconium oxide is zirconium dioxide.

4. A process according to claim 1, in which the amount of the catalyst is from 0.5% to 100% by weight, based on the weight of the glycerol, glycidol, glycerol carbonate or 2,2-dimethyl-1,3-dioxolane-4-methanol.

5. A process according to claim 1, in which the amount of the catalyst is from 1% to 10% by weight, based on the weight of the glycerol, glycidol, glycerol carbonate or 2,2-dimethyl-1,3-dioxolane-4-methanol.

6. A process according to claim 1, in which a reaction temperature of from 150° C. to 350° C. is used.

7. A process according to claim 1, in which a reaction temperature of from 180° C. to 250° C. is used.

8. A process according to claim 1, in which at least 50% by weight (based on the monomer-free reaction mixture) of linear oligomers are formed.

* * * * *